United States Patent [19]

Mason et al.

[11] Patent Number: 4,918,250
[45] Date of Patent: Apr. 17, 1990

[54] PROCESS FOR THE PRODUCTION OF DINITROTOLUENE USING AN INORGANIC SALT AS A PHASE SEPARATION AGENT

[75] Inventors: Robert W. Mason, Lake Charles; Peter C. Imm, Sulphur; Kent J. Bordelon, Lake Charles, all of La.

[73] Assignee: Olin Corporation, Cheshire, Conn.

[21] Appl. No.: 341,447

[22] Filed: Apr. 21, 1989

[51] Int. Cl.$^4$ .............................................. C07C 76/00
[52] U.S. Cl. ..................................... 568/934; 558/488
[58] Field of Search .......................... 568/934; 260/688

[56] References Cited

U.S. PATENT DOCUMENTS

| | | | |
|---|---|---|---|
| 2,362,743 | 11/1944 | Crater | 568/934 |
| 2,739,174 | 3/1956 | Ross | 568/939 |
| 2,864,871 | 12/1958 | Morningstar . | |
| 3,293,310 | 12/1966 | Picard et al. | 568/935 |
| 3,434,802 | 3/1969 | Toischer et al. | 568/934 X |
| 3,780,116 | 12/1973 | Sahgal | 568/939 |
| 3,928,395 | 12/1975 | Seha et al. | 568/939 |
| 3,976,704 | 8/1976 | Vaughan | 568/939 |
| 4,064,147 | 12/1977 | Thelen et al. | 568/939 |
| 4,112,005 | 9/1978 | Thiem et al. | 568/939 X |
| 4,123,466 | 10/1978 | Lin et al. | 568/939 |
| 4,261,908 | 4/1981 | Schroeder et al. | 568/934 X |
| 4,415,744 | 11/1983 | Schumacher et al. | 568/939 X |
| 4,418,230 | 11/1983 | Bakke et al. | 568/939 X |
| 4,426,543 | 1/1984 | Schumacher et al. | 568/939 X |
| 4,465,876 | 8/1984 | Milligan | 568/939 X |
| 4,469,904 | 9/1984 | Wang et al. | 568/939 X |
| 4,551,568 | 11/1985 | Sato et al. | 568/939 |
| 4,600,702 | 7/1986 | Schumacher | 568/939 X |
| 4,618,733 | 10/1986 | Schumacher | 568/939 X |
| 4,621,157 | 11/1986 | McDaniel | 568/934 X |
| 4,628,131 | 12/1986 | Schumacher | 568/939 X |
| 4,804,792 | 2/1989 | Mason et al. | 568/939 |

Primary Examiner—Matthew A. Thexton
Assistant Examiner—Valerie D. Fee
Attorney, Agent, or Firm—Dale Lynn Carlson

[57] ABSTRACT

This invention relates to a process for nitrating toluene to dinitrotoluene and phase separation of the product using an inorganic salt as a phase separation agent.

10 Claims, No Drawings

PROCESS FOR THE PRODUCTION OF DINITROTOLUENE USING AN INORGANIC SALT AS A PHASE SEPARATION AGENT

This invention relates generally to the nitration of toluene and, more specifically, to a process for nitrating toluene to dinitrotoluene employing an inorganic salt as a phase separation agent.

Nitration reactions of aromatic hydrocarbons are generally conducted in mixed acid systems, such as mixed nitric and sulfuric acids. However, these mixed acid systems usually involve reconcentration of the spent sulfuric acid after the nitration reaction. This reconcentration step is time consuming, energy intensive and requires the use of expensive materials of construction. In addition, the use of sulfuric acid tends to result in significant nitrocreosol and cyanide by-product formation, requiring expensive waste-water treatment to remove this by-product from the desired product.

In view of these disadvantages associated with mixed nitric/sulfuric acid systems, there have been various attempts over the years to perform gas phase or liquid phase nitrations in concentrated nitric acid in the absence of sulfuric acid. By way of illustration, U.S. Pat. No. 2,362,743 discloses a two-step process for the manufacture of dinitrotoluene ("DNT") in the absence of sulfuric acid which comprises (a) nitrating toluene to mononitrotoluene using a nitric acid having a concentration of from about 60 percent to about 75 percent and a mole ratio of toluene to nitric acid of about 1 to about 3.5 and (b) nitrating the mononitrotoluene to dinitrotoluene using nitric acid having a concentration of from about 90 percent to about 100 percent, and a mole ratio of mononitrotoluene to nitric acid of about 1 to about 3. Although the process of this '743 patent is advantageously conducted in the absence of sulfuric acid, it has now been found that in step (b), a very high percentage of the nitrated product (up to 25 percent) based upon the amount of toluene reactant employed does not phase separate from the nitric acid medium. Indeed, the '743 patent teaches vacuum distillation of the product mixture to isolate the desired dinitrotoluene, an expensive and highly energy intensive process step.

Since DNT is useful as an intermediate in producing TDI, new processes for the selective manufacture of this intermediate utilizing a more energy efficient phase separation technique would be highly desirable to the polyisocyanate manufacturing community. Heretofore, no process has been disclosed to the knowledge of the present inventors which provides for the nitration of toluene to DNT in the absence of a solvent and in the absence of sulfuric acid while affording enhanced phase separation of the nitrated product from nitric acid without distillation.

The present invention relates to a process for producing DNT by a two-step liquid phase nitration reaction of nitric acid with toluene at a reaction temperature not exceeding 80° C. in the absence of sulfuric acid and in the absence of a solvent.

The process comprises:
(a) reacting toluene with nitric acid having an acid concentration of between about 60 and about 75 percent by weight, based upon the total amount of acid plus water, at a reaction temperature of between about 60° C. and about 75° C., and employing between about 3 and about 5 moles of nitric acid per mole of toluene, to produce mononitrotoluene,
(b) reacting said mononitrotoluene with concentrated nitric acid having an acid concentration of between about 90 and about 100 percent by weight, based upon the total amount of acid plus water therein, at a reaction temperature of between about 40° C. and about 70° C., and employing between about 3 and about 4 moles of concentrated nitric acid per mole of mononitrotoluene, to produce a mixture containing dinitrotoluene and unreacted nitric acid, and
(c) incorporating an inorganic salt into said mixture to cause phase separation of said dinitrotoluene from said unreacted nitric acid in said mixture.

This and other aspects of the present invention will become apparent upon reading the following detailed description of the invention.

The process of the present invention utilizes a two-step reaction in liquid media and does not involve the formation of the two phase emulsions observed in conventional, mixed sulfuric/nitric acid nitration processes or processes which utilize a solvent. Phase separation of the desired dinitrotoluene from the product mixture is suitably effected by adding an inorganic salt to the product mixture. The inorganic salt is preferably soluble in the product mixture.

The inorganic salt is generally incorporated into the mixture of dinitrotoluene and unreacted nitric acid in a "phase separation effective amount", i.e., an amount sufficient to cause phase separation of the mixture in order to facilitate isolation of the dinitritoluene from the unreacted nitric acid in the product mixture. Preferably, the inorganic salt is employed in a molar amount sufficient to provide between 25 percent and 100 percent of a full saturation concentration of said inorganic salt in said nitric acid, where the full saturation concentration is measured at the reaction temperature employed in step (b). For example, when employing magnesium nitrate hexahydrate as the inorganic salt, it is preferred to use between 0.2 gram and 0.85 gram of salt per gram of toluene.

Particularly advantageous inorganic salts are the inorganic sulfates, inorganic nitrates, and combinations thereof. Illustrative inorganic salts are the alkali metal and alkaline earth metal salts such as sodium nitrate, sodium sulfate, potassium sulfate, potassium nitrate, magnesium nitrate hexahydrate, magnesium nitrate trihydrate, and combinations thereof. The preferred inorganic salts are the nitrate salts, more preferably magnesium nitrate hexahydrate. It is preferred to use inorganic salt(s) which are chemically stable in the presence of the step (a) and step (b) reactions. For example, it is preferred not to use chloride salts due to the formation of chlorine and various nitrogen reaction by-products.

The timing of addition of the inorganic salt is not critical and can be effected before, during, or after either step (a) or step (b) of the process of the present invention. For convenience, it is preferred that the inorganic salt be added to the reaction mixture before step (a) even though the inorganic salt is not necessary for phase separation of the mononitrotoluene from the step (a) intermediate reaction. The inorganic salt is then carried over into the step (b) reaction mixture, and is available in the step (b) product mixture to cause phase separation of the highly soluble dinitrotoluene from the product mixture.

The reaction of step (a) is suitably conducted at a reaction temperature not exceeding 80° C., preferably between about 60° C. and about 75° C., more preferably between about 65° C. and about 75° C., most preferably about 70° C. The reaction of step (b) is suitably conducted at a reaction temperature not exceeding 80° C., preferably between about 40° C. and about 70° C., more preferably between about 60° C. and about 70° C., most preferably about 65° C.

The reactions are suitably conducted at atmospheric pressure, although subatmospheric pressure can be employed if desired. The reaction time is typically between one and five hours for each of steps (a) and (b), preferably about two hours for each step.

After phase separation, washing with water and a basic solution produces a purified DNT product. These wash waters are free of the nitrocreosol impurities observed in the wastewater produced in a conventional, mixed sulfuric/nitric acid DNT process. The aqueous nitric acid from the phase separation step can be purified by toluene extraction, the toluene phase being recycled to the step (a) reaction and the 60–70% aqueous nitric acid phase reconcentrated, sold or recycled back into the step (a) reaction.

The following examples are intended to illustrate, but in no way limit the scope of, the present invention.

EXAMPLE 1

Improved Phase Separation of Dinitrotoluene From Nitric Acid Caused by Magnesium Nitrate Hexahydrate A mixture of 82.0 g of 59.5 percent $HNO_3$, 64.6 g of $Mg(NO_3)_2.6H_2O$ and 32.9 g of commercial grade dinitrotoluene (mixture of isomers) was added to a separatory funnel and immersed in a water bath at 69° C. After occasional shaking, to dissolve and disperse the components, the layers were allowed to separate. A heavy acid/salt layer (141.4 g) was drawn off the bottom of the funnel, followed by the lighter DNT layer (36.4 g). After dilution with water and cooling, 2.87 g of dinitrotoluene was recovered from the acid/salt layer equal to 8.7 percent of the original DNT fed.

When an analogous mixture, but without added inorganic salt, was phase separated, dinitrotoluene in the acid phase amounted to 27.6 percent of that which was originally fed.

EXAMPLE 2

Two-Step Reaction to Produce Dinitrotoluene and Phase Separation Using Magnesium Nitrate Hexahydrate A mixture of 92.14 g (1.0 mole) of toluene was reacted with 484.7 g of 65 percent $HNO_3$ (5.0 mole $HNO_3$), in the presence of 412.0 g magnesium nitrite hexahydrate, for two hours at 70° C. in a mechanically agitated, jacketed flask. After phase separation of 133.4 g of mononitrotoluene (MNT) product from 827.0 g of spent nitric acid/magnesium nitrate mixture, the MNT was further reacted with 255.9 g (4.0 moles) of 98.5 percent $HNO_3$ for two hours at 70° C. Vacuum distillation of the reaction product removed 102.8 g of 99.4 percent $HNO_3$, leaving 255.3 g of DNT/aqueous $HNO_3$. This DNT/aqueous $HNO_3$ mixture was combined with the aqueous $HNO_3$/magnesium nitrate mixture from the mononitrate step and phase separated. After washing the DNT with 92.0 g of hot water, 147.4 g of DNT, 895.8 g of $HNO_3$/magnesium nitrate mixture and 119.5 g of wash water were recovered. The wash water and $HNO_3$/magnesium nitrate mixture were diluted with water and chilled to 4° C. to crystallize the DNT content of each solution. The $HNO_3$/magnesium nitrate mixture contained 14.4 g of DNT (8.9 percent of total DNT recovered), while the wash water contained 0.78 g of DNT (0.5 percent).

An identical reaction and phase separation sequence, but without added inorganic salt, gave 97.1 g of DNT, 554.3 g of spent $HNO_3$, containing 68.0 g of DNT (40.9 percent of total DNT recovered) and 136.3 g of wash water, containing 1.35 g of DNT (0.8 percent).

What is claimed is:

1. A process for producing dinitrotoluene and causing phase separation of the dinitrotoluene so produced from the product mixture which comprises:
   (a) reacting toluene with nitric acid having an acid concentration of between about 60 and about 75 percent by weight, based upon the total amount of acid plus water, at a reaction temperature of between about 60° C. and about 75° C., and employing between about 3 and about 5 moles of nitric acid per mole of toluene, to produce mononitrotoluene,
   (b) reacting said mononitrotoluene with concentrated nitric acid having an acid concentration of between about 90 and about 100 percent by weight, based upon the total amount of acid plus water therein, at a reaction temperature of between about 40° C. and about 70° C., and employing between about 3 and about 4 moles of concentrated nitric acid per mole of mononitrotoluene, to produce a mixture containing dinitrotoluene and unreacted nitric acid, and
   (c) incorporating an inorganic salt into said mixture to cause phase separation of said dinitrotoluene from said unreacted nitric acid in said mixture.

2. The process of claim 1 wherein said inorganic salt is selected from the group consisting of inorganic sulfates, inorganic nitrates, and combinations thereof.

3. The process of claim 1 wherein said inorganic salt is selected from the group consisting of sodium nitrate, sodium sulfate, magnesium nitrate hexahydrate, and combinations thereof.

4. The process of claim 1 wherein said inorganic salt is added either before, during, or after step (a) or step (b) in order to incorporate said inorganic salt into said mixture to cause said phase separation.

5. The process of claim 1 wherein said nitric acid of step (a) has an acid concentration of between about 60 and about 70 percent by weight, based upon the total amount of acid plus water.

6. The process of claim 1 wherein said concentrated nitric acid of step (b) has an acid concentration of between about 95 and about 100 percent by weight, based upon the total amount of acid plus water.

7. The process of claim 1 wherein said inorganic salt is added before step (a), and wherein said salt is employed in a molar amount sufficient to provide between 25 percent and 100 percent of a full saturation concentration of said inorganic salt in said nitric acid step (a).

8. The process of claim 1 wherein said inorganic salt is added before step (b), and wherein said inorganic salt is employed in a molar amount sufficient to provide between 25 percent and 100 percent of a full saturation concentration of said inorganic salt in said concentrated nitric acid of step (b).

9. The process of claim 1 wherein step (a) is conducted for a reaction time of between about 1 and about 5 hours.

10. The process of claim 1 wherein step (b) is conducted for a reaction time of between about 1 and about 5 hours.

* * * * *